United States Patent [19]
Reid et al.

[11] Patent Number: 5,731,154
[45] Date of Patent: Mar. 24, 1998

[54] METHOD FOR DETECTING HUMAN CONTACTIN

[75] Inventors: Robert Alan Reid, Durham; John Jacob Hemperly, Apex, both of N.C.

[73] Assignee: Becton, Dickinson and Company, Franklin Lakes, N.J.

[21] Appl. No.: 408,420

[22] Filed: Mar. 21, 1995

Related U.S. Application Data

[62] Division of Ser. No. 40,741, Mar. 26, 1993.

[51] Int. Cl.$^6$ .......................... G01N 33/53; G01N 33/537
[52] U.S. Cl. .................. 435/7.1; 435/7.92; 435/240.27
[58] Field of Search ................................. 435/7.1, 7.92, 435/240.27; 530/387.1, 388.1

[56] References Cited

PUBLICATIONS

Berglund et al, 1991a, Brain Res. 549:292–296.
Berglund et al, 1991b, Eur. J. Biochem 197:549–554.
Ranscht et al, 1988, J. Cell Biol 107:1561–1573.
Gennarini et al, 1989, J. Cell Biol 109:775–788.

*Primary Examiner*—Lila Feisee
*Assistant Examiner*—Ray F. Ebert
*Attorney, Agent, or Firm*—Donna R. Fugit

[57] ABSTRACT

A human brain glycoprotein homologous to the mouse F3 and the chicken contactin/F11 adhesion molecules is provided. Also described are nucleic acid sequences encoding the human brain glycoprotein and antibodies directed against the human brain glycoprotein.

5 Claims, 1 Drawing Sheet

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:

(A) ORGANISM: Mouse (xi) SEQUENCE DESCRIPTION: SEQ ID NO:1:

TAGACCGGAT GGCCAACA                                                                                           18

(2) INFORMATION FOR SEQ ID NO:2:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: YES (vi) ORIGINAL SOURCE:
  (A) ORGANISM: Mouse (xi) SEQUENCE DESCRIPTION: SEQ ID NO:2:

CTCGACAACA TACTCTCC                                                                                           18

(2) INFORMATION FOR SEQ ID NO:3:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: NO (vi) ORIGINAL SOURCE:
  (A) ORGANISM: Mouse (xi) SEQUENCE DESCRIPTION: SEQ ID NO:3:

CTCTGGTGAT CACAAATC                                                                                           18

(2) INFORMATION FOR SEQ ID NO:4:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: YES (vi) ORIGINAL SOURCE:
  (A) ORGANISM: Mouse (xi) SEQUENCE DESCRIPTION: SEQ ID NO:4:

TCATCTGAGA GAATCGTC                                                                                           18

(2) INFORMATION FOR SEQ ID NO:5:

(i) SEQUENCE CHARACTERISTICS:
  (A) LENGTH: 3360 base pairs
  (B) TYPE: nucleic acid
  (C) STRANDEDNESS: both
  (D) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( i x ) FEATURE:
    ( A ) NAME/KEY: CDS
    ( B ) LOCATION: 122..3175

( i x ) FEATURE:
    ( A ) NAME/KEY: mat_peptide
    ( B ) LOCATION: 182..3100

( i x ) FEATURE:
    ( A ) NAME/KEY: sig_peptide
    ( B ) LOCATION: 122..181

( i x ) FEATURE:
    ( A ) NAME/KEY: 5'UTR
    ( B ) LOCATION: 10..121

( i x ) FEATURE:
    ( A ) NAME/KEY: 3'UTR
    ( B ) LOCATION: 3176..3360

( i x ) FEATURE:
    ( A ) NAME/KEY: polyA_site
    ( B ) LOCATION: 3281..3286

( i x ) FEATURE:
    ( A ) NAME/KEY: misc_feature
    ( B ) LOCATION: 1..9
    ( D ) OTHER INFORMATION: /function="EcoRI cloning linker"
        / product="none"

( i x ) FEATURE:
    ( A ) NAME/KEY: misc_feature
    ( B ) LOCATION: 3101..3175
    ( D ) OTHER INFORMATION: /function="Attachment to
        glycolipid"
        / product="COOH-signal peptide"

( x i ) SEQUENCE DESCRIPTION: SEQ ID NO:5:

```
GAATTCCGGC TGTGCCGCAC CGAGGCGAGC AGGAGCAGGG AACAGGTGTT TAAAATTATC        60

CAACTGCCAT AGAGCTAAAT TCTTTTTTGG AAAATTGAAC CGAACTTCTA CTGAATACAA       120

G ATG AAA ATG TGG TTG CTG GTC AGT CAT CTT GTG ATA ATA TCT ATT          166
  Met Lys Met Trp Leu Leu Val Ser His Leu Val Ile Ile Ser Ile
  -20             -15                 -10

ACT ACC TGT TTA GCA GAG TTT ACA TGG TAT AGA AGA TAT GGT CAT GGA        214
Thr Thr Cys Leu Ala Glu Phe Thr Trp Tyr Arg Arg Tyr Gly His Gly
 -5              1                   5                    10

GTT TCT GAG GAA GAC AAA GGA TTT GGA CCA ATT TTT GAA GAG CAG CCA        262
Val Ser Glu Glu Asp Lys Gly Phe Gly Pro Ile Phe Glu Glu Gln Pro
             15                  20                  25

ATC AAT ACC ATT TAT CCA GAG GAA TCA CTG GAA GGA AAA GTC TCA CTC        310
Ile Asn Thr Ile Tyr Pro Glu Glu Ser Leu Glu Gly Lys Val Ser Leu
         30                  35                  40

AAC TGT AGG GCA CGA GCC AGC CCT TTC CCG GTT TAC AAA TGG AGA ATG        358
Asn Cys Arg Ala Arg Ala Ser Pro Phe Pro Val Tyr Lys Trp Arg Met
     45                  50                  55

AAT AAT GGG GAC GTT GAT CTC ACA AGT GAT CGA TAC AGT ATG GTA GGA        406
Asn Asn Gly Asp Val Asp Leu Thr Ser Asp Arg Tyr Ser Met Val Gly
 60                  65                  70                  75

GGA AAC CTT GTT ATC AAC AAC CCT GAC AAA CAG AAA GAT GCT GGA ATA        454
Gly Asn Leu Val Ile Asn Asn Pro Asp Lys Gln Lys Asp Ala Gly Ile
             80                  85                  90
```

-continued

| | | | | | | | | | | | | | | | | |
|---|---|---|---|---|---|---|---|---|---|---|---|---|---|---|---|---|
| TAC | TAC | TGT | TTA | GCA | TCT | AAT | AAC | TAC | GGG | ATG | GTC | AGA | AGC | ACT | GAA | 502 |
| Tyr | Tyr | Cys | Leu | Ala | Ser | Asn | Asn | Tyr | Gly | Met | Val | Arg | Ser | Thr | Glu | |
| | | | 95 | | | | | 100 | | | | | 105 | | | |
| GCA | ACC | CTG | AGC | TTT | GGA | TAT | CTT | GAT | CCT | TTC | CCA | CCT | GAG | GAA | CGT | 550 |
| Ala | Thr | Leu | Ser | Phe | Gly | Tyr | Leu | Asp | Pro | Phe | Pro | Pro | Glu | Glu | Arg | |
| | | 110 | | | | | 115 | | | | 120 | | | | | |
| CCT | GAG | GTC | AGA | GTA | AAA | GAA | GGG | AAA | GGA | ATG | GTG | CTT | CTC | TGT | GAC | 598 |
| Pro | Glu | Val | Arg | Val | Lys | Glu | Gly | Lys | Gly | Met | Val | Leu | Leu | Cys | Asp | |
| | 125 | | | | | 130 | | | | | 135 | | | | | |
| CCC | CCA | TAC | CAT | TTT | CCA | GAT | GAT | CTT | AGC | TAT | CGC | TGG | CTT | CTA | AAT | 646 |
| Pro | Pro | Tyr | His | Phe | Pro | Asp | Asp | Leu | Ser | Tyr | Arg | Trp | Leu | Leu | Asn | |
| 140 | | | | | 145 | | | | | 150 | | | | | 155 | |
| GAA | TTT | CCT | GTA | TTT | ATC | ACA | ATG | GAT | AAA | CGG | CGA | TTT | GTG | TCT | CAG | 694 |
| Glu | Phe | Pro | Val | Phe | Ile | Thr | Met | Asp | Lys | Arg | Arg | Phe | Val | Ser | Gln | |
| | | | | 160 | | | | | 165 | | | | | 170 | | |
| ACA | AAT | GGC | AAT | CTC | TAC | ATT | GCA | AAT | GTT | GAG | GCT | TCC | GAC | AAA | GGC | 742 |
| Thr | Asn | Gly | Asn | Leu | Tyr | Ile | Ala | Asn | Val | Glu | Ala | Ser | Asp | Lys | Gly | |
| | | | 175 | | | | | 180 | | | | | 185 | | | |
| AAT | TAT | TCC | TGC | TTT | GTT | TCC | AGT | CCT | TCT | ATT | ACA | AAG | AGC | GTG | TTC | 790 |
| Asn | Tyr | Ser | Cys | Phe | Val | Ser | Ser | Pro | Ser | Ile | Thr | Lys | Ser | Val | Phe | |
| | | 190 | | | | | 195 | | | | | 200 | | | | |
| AGC | AAA | TTC | ATC | CCA | CTC | ATT | CCA | ATA | CCT | GAA | CGA | ACA | ACA | AAA | CCA | 838 |
| Ser | Lys | Phe | Ile | Pro | Leu | Ile | Pro | Ile | Pro | Glu | Arg | Thr | Thr | Lys | Pro | |
| | 205 | | | | | 210 | | | | | 215 | | | | | |
| TAT | CCT | GCT | GAT | ATT | GTA | GTT | CAG | TTC | AAG | GAT | GTA | TAT | GCA | TTG | ATG | 886 |
| Tyr | Pro | Ala | Asp | Ile | Val | Val | Gln | Phe | Lys | Asp | Val | Tyr | Ala | Leu | Met | |
| 220 | | | | | 225 | | | | | 230 | | | | | 235 | |
| GGC | CAA | AAT | GTG | ACC | TTA | GAA | TGT | TTT | GCA | CTT | GGA | AAT | CCT | GTT | CCG | 934 |
| Gly | Gln | Asn | Val | Thr | Leu | Glu | Cys | Phe | Ala | Leu | Gly | Asn | Pro | Val | Pro | |
| | | | | 240 | | | | | 245 | | | | | 250 | | |
| GAT | ATC | CGA | TGG | CGG | AAG | GTT | CTA | GAA | CCA | ATG | CCA | AGC | ACT | GCT | GAG | 982 |
| Asp | Ile | Arg | Trp | Arg | Lys | Val | Leu | Glu | Pro | Met | Pro | Ser | Thr | Ala | Glu | |
| | | | 255 | | | | | 260 | | | | | 265 | | | |
| ATT | AGC | ACC | TCT | GGG | GCT | GTT | CTT | AAG | ATC | TTC | AAT | ATT | CAG | CTA | GAA | 1030 |
| Ile | Ser | Thr | Ser | Gly | Ala | Val | Leu | Lys | Ile | Phe | Asn | Ile | Gln | Leu | Glu | |
| | | 270 | | | | | 275 | | | | | 280 | | | | |
| GAT | GAA | GGC | ATC | TAT | GAA | TGT | GAG | GCT | GAG | AAC | ATT | AGA | GGA | AAG | GAT | 1078 |
| Asp | Glu | Gly | Ile | Tyr | Glu | Cys | Glu | Ala | Glu | Asn | Ile | Arg | Gly | Lys | Asp | |
| | 285 | | | | | 290 | | | | | 295 | | | | | |
| AAA | CAT | CAA | GCA | AGA | ATT | TAT | GTT | CAA | GCA | TTC | CCT | GAG | TGG | GTA | GAA | 1126 |
| Lys | His | Gln | Ala | Arg | Ile | Tyr | Val | Gln | Ala | Phe | Pro | Glu | Trp | Val | Glu | |
| 300 | | | | | 305 | | | | | 310 | | | | | 315 | |
| CAC | ATC | AAT | GAC | ACA | GAG | GTG | GAC | ATA | GGC | AGT | GAT | CTC | TAC | TGG | CCT | 1174 |
| His | Ile | Asn | Asp | Thr | Glu | Val | Asp | Ile | Gly | Ser | Asp | Leu | Tyr | Trp | Pro | |
| | | | | 320 | | | | | 325 | | | | | 330 | | |
| TGT | GTG | GCC | ACA | GGA | AAG | CCC | ATC | CCT | ACA | ATC | CGA | TGG | TTG | AAA | AAT | 1222 |
| Cys | Val | Ala | Thr | Gly | Lys | Pro | Ile | Pro | Thr | Ile | Arg | Trp | Leu | Lys | Asn | |
| | | | 335 | | | | | 340 | | | | | 345 | | | |
| GGA | TAT | GCG | TAT | CAT | AAA | GGG | GAA | TTA | AGA | CTG | TAT | GAT | GTG | ACT | TTT | 1270 |
| Gly | Tyr | Ala | Tyr | His | Lys | Gly | Glu | Leu | Arg | Leu | Tyr | Asp | Val | Thr | Phe | |
| | | 350 | | | | | 355 | | | | | 360 | | | | |
| GAA | AAT | GCC | GGA | ATG | TAT | CAG | TGC | ATA | GCT | GAA | AAC | ACA | TAT | GGA | GCC | 1318 |
| Glu | Asn | Ala | Gly | Met | Tyr | Gln | Cys | Ile | Ala | Glu | Asn | Thr | Tyr | Gly | Ala | |
| | 365 | | | | | 370 | | | | | 375 | | | | | |
| ATT | TAT | GCA | AAT | GCT | GAG | TTG | AAG | ATC | TTG | GCG | TTG | GCT | CCA | ACT | TTT | 1366 |
| Ile | Tyr | Ala | Asn | Ala | Glu | Leu | Lys | Ile | Leu | Ala | Leu | Ala | Pro | Thr | Phe | |
| 380 | | | | | 385 | | | | | 390 | | | | | 395 | |
| GAA | ATG | AAT | CCT | ATG | AAG | AAA | AAG | ATC | CTG | GCT | GCT | AAA | GGT | GGA | AGG | 1414 |
| Glu | Met | Asn | Pro | Met | Lys | Lys | Lys | Ile | Leu | Ala | Ala | Lys | Gly | Gly | Arg | |
| | | | | 400 | | | | | 405 | | | | | 410 | | |

-continued

| | | | | | | | | | | | | | | | | |
|---|---|---|---|---|---|---|---|---|---|---|---|---|---|---|---|---|
| GTG | ATA | ATT | GAA | TGC | AAA | CCT | AAA | GCT | GCA | CCG | AAA | CCA | AAG | TTT | TCA | 1462 |
| Val | Ile | Ile | Glu | Cys | Lys | Pro | Lys | Ala | Ala | Pro | Lys | Pro | Lys | Phe | Ser | |
| | | | 415 | | | | | 420 | | | | | 425 | | | |
| TGG | AGT | AAA | GGG | ACA | GAG | TGG | CTT | GTC | AAT | AGC | AGC | AGA | ATA | CTC | ATT | 1510 |
| Trp | Ser | Lys | Gly | Thr | Glu | Trp | Leu | Val | Asn | Ser | Ser | Arg | Ile | Leu | Ile | |
| | | 430 | | | | | 435 | | | | | 440 | | | | |
| TGG | GAA | GAT | GGT | AGC | TTG | GAA | ATC | AAC | AAC | ATT | ACA | AGG | AAT | GAT | GGA | 1558 |
| Trp | Glu | Asp | Gly | Ser | Leu | Glu | Ile | Asn | Asn | Ile | Thr | Arg | Asn | Asp | Gly | |
| | 445 | | | | | 450 | | | | | 455 | | | | | |
| GGT | ATC | TAT | ACA | TGC | TTT | GCA | GAA | AAT | AAC | AGA | GGG | AAA | GCT | AAT | AGC | 1606 |
| Gly | Ile | Tyr | Thr | Cys | Phe | Ala | Glu | Asn | Asn | Arg | Gly | Lys | Ala | Asn | Ser | |
| 460 | | | | | 465 | | | | | 470 | | | | | 475 | |
| ACT | GGA | ACC | CTT | GTT | ATC | ACA | GAT | CCT | ACG | CGA | ATT | ATA | TTG | GCC | CCA | 1654 |
| Thr | Gly | Thr | Leu | Val | Ile | Thr | Asp | Pro | Thr | Arg | Ile | Ile | Leu | Ala | Pro | |
| | | | | 480 | | | | | 485 | | | | | 490 | | |
| ATT | AAT | GCC | GAT | ATC | ACA | GTT | GGA | GAA | AAC | GCC | ACC | ATG | CAG | TGT | GCT | 1702 |
| Ile | Asn | Ala | Asp | Ile | Thr | Val | Gly | Glu | Asn | Ala | Thr | Met | Gln | Cys | Ala | |
| | | | 495 | | | | | 500 | | | | | 505 | | | |
| GCG | TCC | TTT | GAT | CCT | GCC | TTG | GAT | CTC | ACA | TTT | GTT | TGG | TCC | TTC | AAT | 1750 |
| Ala | Ser | Phe | Asp | Pro | Ala | Leu | Asp | Leu | Thr | Phe | Val | Trp | Ser | Phe | Asn | |
| | | 510 | | | | | 515 | | | | | 520 | | | | |
| GGC | TAT | GTG | ATC | GAT | TTT | AAC | AAA | GAG | AAT | ATT | CAC | TAC | CAG | AGG | AAT | 1798 |
| Gly | Tyr | Val | Ile | Asp | Phe | Asn | Lys | Glu | Asn | Ile | His | Tyr | Gln | Arg | Asn | |
| | 525 | | | | | 530 | | | | | 535 | | | | | |
| TTT | ATG | CTG | GAT | TCC | AAT | GGG | GAA | TTA | CTA | ATC | CGA | AAT | GCG | CAG | CTG | 1846 |
| Phe | Met | Leu | Asp | Ser | Asn | Gly | Glu | Leu | Leu | Ile | Arg | Asn | Ala | Gln | Leu | |
| 540 | | | | | 545 | | | | | 550 | | | | | 555 | |
| AAA | CAT | GCT | GGA | AGA | TAC | ACA | TGC | ACT | GCC | CAG | ACA | ATT | GTG | GAC | AAT | 1894 |
| Lys | His | Ala | Gly | Arg | Tyr | Thr | Cys | Thr | Ala | Gln | Thr | Ile | Val | Asp | Asn | |
| | | | | 560 | | | | | 565 | | | | | 570 | | |
| TCT | TCA | GCT | TCA | GCT | GAC | CTT | GTA | GTG | AGA | GGC | CCT | CCA | GGC | CCT | CCA | 1942 |
| Ser | Ser | Ala | Ser | Ala | Asp | Leu | Val | Val | Arg | Gly | Pro | Pro | Gly | Pro | Pro | |
| | | | 575 | | | | | 580 | | | | | 585 | | | |
| GGT | GGT | CTG | AGA | ATA | GAA | GAC | ATT | AGA | GCC | ACT | TCT | GTG | GCA | CTT | ACT | 1990 |
| Gly | Gly | Leu | Arg | Ile | Glu | Asp | Ile | Arg | Ala | Thr | Ser | Val | Ala | Leu | Thr | |
| | | 590 | | | | | 595 | | | | | 600 | | | | |
| TGG | AGC | CGT | GGT | TCA | GAC | AAT | CAT | AGT | CCT | ATT | TCT | AAA | TAC | ACT | ATC | 2038 |
| Trp | Ser | Arg | Gly | Ser | Asp | Asn | His | Ser | Pro | Ile | Ser | Lys | Tyr | Thr | Ile | |
| | 605 | | | | | 610 | | | | | 615 | | | | | |
| CAG | ACC | AAG | ACT | ATT | CTT | TCA | GAT | GAC | TGG | AAA | GAT | GCA | AAG | ACA | GAT | 2086 |
| Gln | Thr | Lys | Thr | Ile | Leu | Ser | Asp | Asp | Trp | Lys | Asp | Ala | Lys | Thr | Asp | |
| 620 | | | | | 625 | | | | | 630 | | | | | 635 | |
| CCC | CCA | ATT | ATT | GAA | GGA | AAT | ATG | GAG | GCA | GCA | AGA | GCA | GTG | GAC | TTA | 2134 |
| Pro | Pro | Ile | Ile | Glu | Gly | Asn | Met | Glu | Ala | Ala | Arg | Ala | Val | Asp | Leu | |
| | | | | 640 | | | | | 645 | | | | | 650 | | |
| ATC | CCA | TGG | ATG | GAG | TAT | GAA | TTC | CGC | GTG | GTA | GCA | ACC | AAT | ACA | CTG | 2182 |
| Ile | Pro | Trp | Met | Glu | Tyr | Glu | Phe | Arg | Val | Val | Ala | Thr | Asn | Thr | Leu | |
| | | | 655 | | | | | 660 | | | | | 665 | | | |
| GGT | AGA | GGA | GAG | CCC | AGT | ATA | CCA | TCT | AAC | AGA | ATT | AAA | ACA | GAC | GGT | 2230 |
| Gly | Arg | Gly | Glu | Pro | Ser | Ile | Pro | Ser | Asn | Arg | Ile | Lys | Thr | Asp | Gly | |
| | | 670 | | | | | 675 | | | | | 680 | | | | |
| GCT | GCA | CCA | AAT | GTG | GCT | CCT | TCA | GAT | GTA | GGA | GGT | GGA | GGT | GGA | AGA | 2278 |
| Ala | Ala | Pro | Asn | Val | Ala | Pro | Ser | Asp | Val | Gly | Gly | Gly | Gly | Gly | Arg | |
| | 685 | | | | | 690 | | | | | 695 | | | | | |
| AAC | AGA | GAG | CTG | ACC | ATA | ACA | TGG | GCG | CCT | TTG | TCA | AGA | GAA | TAC | CAC | 2326 |
| Asn | Arg | Glu | Leu | Thr | Ile | Thr | Trp | Ala | Pro | Leu | Ser | Arg | Glu | Tyr | His | |
| 700 | | | | | 705 | | | | | 710 | | | | | 715 | |
| TAT | GGC | AAC | AAT | TTT | GGT | TAC | ATA | GTG | GCA | TTT | AAG | CCA | TTT | GAT | GGA | 2374 |
| Tyr | Gly | Asn | Asn | Phe | Gly | Tyr | Ile | Val | Ala | Phe | Lys | Pro | Phe | Asp | Gly | |
| | | | | 720 | | | | | 725 | | | | | 730 | | |

```
GAA GAA TGG AAA AAA GTC ACA GTT ACT AAT CCT GAT ACT GGC CGA TAT              2422
Glu Glu Trp Lys Lys Val Thr Val Thr Asn Pro Asp Thr Gly Arg Tyr
            735                 740                 745

GTC CAT AAA GAT GAA ACC ATG AGC CCT TCC ACT GCA TTT CAA GTT AAA              2470
Val His Lys Asp Glu Thr Met Ser Pro Ser Thr Ala Phe Gln Val Lys
        750                 755                 760

GTC AAG GCC TTC AAC AAC AAA GGA GAT GGA CCT TAC AGC CTA CTA GCA              2518
Val Lys Ala Phe Asn Asn Lys Gly Asp Gly Pro Tyr Ser Leu Leu Ala
    765                 770                 775

GTC ATT AAT TCA GCA CAA GAC GCT CCC AGT GAA GCC CCA ACA GAA GTA              2566
Val Ile Asn Ser Ala Gln Asp Ala Pro Ser Glu Ala Pro Thr Glu Val
780                 785                 790                 795

GGT GTA AAA GTC TTA TCA TCT TCT GAG ATA TCT GTT CAT TGG GAA CAT              2614
Gly Val Lys Val Leu Ser Ser Ser Glu Ile Ser Val His Trp Glu His
                800                 805                 810

GTT TTA GAA AAA ATA GTG GAA AGC TAT CAG ATT CGG TAT TGG GCT GCC              2662
Val Leu Glu Lys Ile Val Glu Ser Tyr Gln Ile Arg Tyr Trp Ala Ala
            815                 820                 825

CAT GAC AAA GAA GAA GCT GCA AAC AGA GTT CAA GTC ACC AGC CAA GAG              2710
His Asp Lys Glu Glu Ala Ala Asn Arg Val Gln Val Thr Ser Gln Glu
        830                 835                 840

TAC TCG GCC AGG CTC GAG AAC CTT CTG CCA GAC ACC CAG TAT TTT ATA              2758
Tyr Ser Ala Arg Leu Glu Asn Leu Leu Pro Asp Thr Gln Tyr Phe Ile
    845                 850                 855

GAA GTC GGG GCC TGC AAT AGT GCA GGG TGT GGA CCT CCA AGT GAC ATG              2806
Glu Val Gly Ala Cys Asn Ser Ala Gly Cys Gly Pro Pro Ser Asp Met
860                 865                 870                 875

ATT GAG GCT TTC ACC AAG AAA GCA CCT CCT AGC CAG CCT CCA AGG ATC              2854
Ile Glu Ala Phe Thr Lys Lys Ala Pro Pro Ser Gln Pro Pro Arg Ile
                880                 885                 890

ATC AGT TCA GTA AGG TCT GGT TCA CGC TAT ATA ATC ACC TGG GAT CAT              2902
Ile Ser Ser Val Arg Ser Gly Ser Arg Tyr Ile Ile Thr Trp Asp His
            895                 900                 905

GTC GTT GCA CTA TCA AAT GAA TCT ACA GTG ACG GGA TAT AAG GTA CTC              2950
Val Val Ala Leu Ser Asn Glu Ser Thr Val Thr Gly Tyr Lys Val Leu
        910                 915                 920

TAC AGA CCT GAT GGC CAG CAT GAT GGC AAG CTG TAT TCA ACT CAC AAA              2998
Tyr Arg Pro Asp Gly Gln His Asp Gly Lys Leu Tyr Ser Thr His Lys
    925                 930                 935

CAC TCC ATA GAA GTC CCA ATC CCC AGA GAT GGA GAA TAC GTT GTG GAG              3046
His Ser Ile Glu Val Pro Ile Pro Arg Asp Gly Glu Tyr Val Val Glu
940                 945                 950                 955

GTT CGC GCG CAC AGT GAT GGA GGA GAT GGA GTG GTG TCT CAA GTC AAA              3094
Val Arg Ala His Ser Asp Gly Gly Asp Gly Val Val Ser Gln Val Lys
                960                 965                 970

ATT TCA GGT GCA CCC ACC CTA TCC CCA AGT CTT CTC GGC TTA CTG CTG              3142
Ile Ser Gly Ala Pro Thr Leu Ser Pro Ser Leu Leu Gly Leu Leu Leu
            975                 980                 985

CCT GCC TTT GGC ATC CTT GTC TAC TTG GAA TTC TGAATGTGTT GTGACAGCTG            3195
Pro Ala Phe Gly Ile Leu Val Tyr Leu Glu Phe
        990                 995

CTGTTCCCAT CCCAGCTCAG AAGACACCCT TCAACCCTGG GATGACCACA ATTCCTTCCA           3255

ATTTCTGCGG CTCCATCCTA AGCCAAATAA ATTATACTTT AACAAACTAT TCAACTGATT           3315

TACAACACAC ATGATGACTG AGGCATTCAG GAACCCCTTC ATCCA                           3360
```

( 2 ) INFORMATION FOR SEQ ID NO:6:

( i ) SEQUENCE CHARACTERISTICS:
        ( A ) LENGTH: 1018 amino acids

```
            ( B ) TYPE: amino acid
            ( D ) TOPOLOGY: linear ( i i ) MOLECULE TYPE: protein ( v i ) ORIGINAL SOURCE:
            ( A ) ORGANISM: Homo sapiens ( i x ) FEATURE:
            ( A ) NAME/KEY: Disulfide-bond
            ( B ) LOCATION: 45..94

( i x ) FEATURE:
            ( A ) NAME/KEY: Disulfide-bond
            ( B ) LOCATION: 138..191

( i x ) FEATURE:
            ( A ) NAME/KEY: Disulfide-bond
            ( B ) LOCATION: 243..290

( i x ) FEATURE:
            ( A ) NAME/KEY: Disulfide-bond
            ( B ) LOCATION: 332..371

( i x ) FEATURE:
            ( A ) NAME/KEY: Disulfide-bond
            ( B ) LOCATION: 416..464

( i x ) FEATURE:
            ( A ) NAME/KEY: Disulfide-bond
            ( B ) LOCATION: 506..563

( i x ) FEATURE:
            ( A ) NAME/KEY: Domain
            ( B ) LOCATION: 604..657
            ( D ) OTHER INFORMATION: /label=FLR
                    / note="conserved core of fibronectin type
                    III-like repeat"

( i x ) FEATURE:
            ( A ) NAME/KEY: Domain
            ( B ) LOCATION: 707..760
            ( D ) OTHER INFORMATION: /label=FLR
                    / note="conserved core of fibronectin type
                    III-like repeat"

( i x ) FEATURE:
            ( A ) NAME/KEY: Domain
            ( B ) LOCATION: 809..857
            ( D ) OTHER INFORMATION: /label=FLR
                    / note="conserved core of fibronectin type
                    III-like repeat"

( i x ) FEATURE:
            ( A ) NAME/KEY: Domain
            ( B ) LOCATION: 905..952
            ( D ) OTHER INFORMATION: /label=FLR
                    / note="conserved core of fibronectin type
                    III-like repeat"

( i x ) FEATURE:
            ( A ) NAME/KEY: Modified-site
            ( B ) LOCATION: 188
            ( D ) OTHER INFORMATION: /label=ASN-glycos
                    / note="potential site of ASN-linked
                    glycosylation"

( i x ) FEATURE:
            ( A ) NAME/KEY: Modified-site
            ( B ) LOCATION: 238
            ( D ) OTHER INFORMATION: /label=ASN-glycos
                    / note="potential site of ASN-linked
                    glycosylation"

( i x ) FEATURE:
            ( A ) NAME/KEY: Modified-site
            ( B ) LOCATION: 318
            ( D ) OTHER INFORMATION: /label=ASN-glycos
                    / note="potential site of ASN-linked
                    glycosylation"
```

( i x ) FEATURE:
    ( A ) NAME/KEY: Modified-site
    ( B ) LOCATION: 437
    ( D ) OTHER INFORMATION: /label=ASN-glycos
        / note="potential site of ASN-linked glycosylation"

( i x ) FEATURE:
    ( A ) NAME/KEY: Modified-site
    ( B ) LOCATION: 453
    ( D ) OTHER INFORMATION: /label=ASN-glycos
        / note="potential site of ASN-linked glycosylation"

( i x ) FEATURE:
    ( A ) NAME/KEY: Modified-site
    ( B ) LOCATION: 474
    ( D ) OTHER INFORMATION: /label=ASN-glycos
        / note="potential site of ASN-linked glycosylation"

( i x ) FEATURE:
    ( A ) NAME/KEY: Modified-site
    ( B ) LOCATION: 501
    ( D ) OTHER INFORMATION: /label=ASN-glycos
        / note="potential site of ASN-linked glycosylation"

( i x ) FEATURE:
    ( A ) NAME/KEY: Modified-site
    ( B ) LOCATION: 571
    ( D ) OTHER INFORMATION: /label=ASN-glycos
        / note="potential site of ASN-linked glycosylation"

( i x ) FEATURE:
    ( A ) NAME/KEY: Modified-site
    ( B ) LOCATION: 913
    ( D ) OTHER INFORMATION: /label=ASN-glycos
        / note="potential site of ASN-linked glycosylation"

( x i ) SEQUENCE DESCRIPTION: SEQ ID NO:6:

```
Met Lys Met Trp Leu Leu Val Ser His Leu Val Ile Ile Ser Ile Thr
-20              -15              -10                       -5

Thr Cys Leu Ala Glu Phe Thr Trp Tyr Arg Arg Tyr Gly His Gly Val
                 1           5                    10

Ser Glu Glu Asp Lys Gly Phe Gly Pro Ile Phe Glu Glu Gln Pro Ile
         15              20                   25

Asn Thr Ile Tyr Pro Glu Glu Ser Leu Glu Gly Lys Val Ser Leu Asn
     30              35                40

Cys Arg Ala Arg Ala Ser Pro Phe Pro Val Tyr Lys Trp Arg Met Asn
45                  50              55                       60

Asn Gly Asp Val Asp Leu Thr Ser Asp Arg Tyr Ser Met Val Gly Gly
             65                  70                       75

Asn Leu Val Ile Asn Asn Pro Asp Lys Gln Lys Asp Ala Gly Ile Tyr
             80              85                  90

Tyr Cys Leu Ala Ser Asn Asn Tyr Gly Met Val Arg Ser Thr Glu Ala
         95              100                 105

Thr Leu Ser Phe Gly Tyr Leu Asp Pro Phe Pro Pro Glu Glu Arg Pro
    110                 115             120

Glu Val Arg Val Lys Glu Gly Lys Gly Met Val Leu Leu Cys Asp Pro
125                 130             135                      140

Pro Tyr His Phe Pro Asp Asp Leu Ser Tyr Arg Trp Leu Leu Asn Glu
             145                 150                 155

Phe Pro Val Phe Ile Thr Met Asp Lys Arg Arg Phe Val Ser Gln Thr
             160             165                 170
```

-continued

| | | | | | | | | | | | | | | |
|---|---|---|---|---|---|---|---|---|---|---|---|---|---|---|
| Asn | Gly | Asn 175 | Leu | Tyr | Ile | Ala | Asn 180 | Val | Glu | Ala | Ser | Asp 185 | Lys | Gly | Asn |
| Tyr | Ser 190 | Cys | Phe | Val | Ser | Ser 195 | Pro | Ser | Ile | Thr | Lys 200 | Ser | Val | Phe | Ser |
| Lys 205 | Phe | Ile | Pro | Leu | Ile 210 | Pro | Ile | Pro | Glu | Arg 215 | Thr | Thr | Lys | Pro | Tyr 220 |
| Pro | Ala | Asp | Ile | Val 225 | Val | Gln | Phe | Lys | Asp 230 | Val | Tyr | Ala | Leu | Met 235 | Gly |
| Gln | Asn | Val | Thr 240 | Leu | Glu | Cys | Phe | Ala 245 | Leu | Gly | Asn | Pro | Val 250 | Pro | Asp |
| Ile | Arg | Trp 255 | Arg | Lys | Val | Leu | Glu 260 | Pro | Met | Pro | Ser | Thr 265 | Ala | Glu | Ile |
| Ser | Thr 270 | Ser | Gly | Ala | Val | Leu 275 | Lys | Ile | Phe | Asn | Ile 280 | Gln | Leu | Glu | Asp |
| Glu 285 | Gly | Ile | Tyr | Glu | Cys 290 | Glu | Ala | Glu | Asn | Ile 295 | Arg | Gly | Lys | Asp | Lys 300 |
| His | Gln | Ala | Arg | Ile 305 | Tyr | Val | Gln | Ala | Phe 310 | Pro | Glu | Trp | Val | Glu 315 | His |
| Ile | Asn | Asp | Thr 320 | Glu | Val | Asp | Ile | Gly 325 | Ser | Asp | Leu | Tyr | Trp 330 | Pro | Cys |
| Val | Ala | Thr 335 | Gly | Lys | Pro | Ile | Pro 340 | Thr | Ile | Arg | Trp | Leu 345 | Lys | Asn | Gly |
| Tyr | Ala 350 | Tyr | His | Lys | Gly | Glu 355 | Leu | Arg | Leu | Tyr | Asp 360 | Val | Thr | Phe | Glu |
| Asn 365 | Ala | Gly | Met | Tyr | Gln 370 | Cys | Ile | Ala | Glu | Asn 375 | Thr | Tyr | Gly | Ala | Ile 380 |
| Tyr | Ala | Asn | Ala | Glu 385 | Leu | Lys | Ile | Leu | Ala 390 | Leu | Ala | Pro | Thr | Phe 395 | Glu |
| Met | Asn | Pro | Met 400 | Lys | Lys | Lys | Ile | Leu 405 | Ala | Ala | Lys | Gly | Gly 410 | Arg | Val |
| Ile | Ile | Glu 415 | Cys | Lys | Pro | Lys | Ala 420 | Ala | Pro | Lys | Pro | Lys 425 | Phe | Ser | Trp |
| Ser | Lys 430 | Gly | Thr | Glu | Trp | Leu 435 | Val | Asn | Ser | Ser | Arg 440 | Ile | Leu | Ile | Trp |
| Glu 445 | Asp | Gly | Ser | Leu | Glu 450 | Ile | Asn | Asn | Ile | Thr 455 | Arg | Asn | Asp | Gly | Gly 460 |
| Ile | Tyr | Thr | Cys | Phe 465 | Ala | Glu | Asn | Asn | Arg 470 | Gly | Lys | Ala | Asn | Ser 475 | Thr |
| Gly | Thr | Leu | Val 480 | Ile | Thr | Asp | Pro | Thr 485 | Arg | Ile | Ile | Leu | Ala 490 | Pro | Ile |
| Asn | Ala | Asp 495 | Ile | Thr | Val | Gly | Glu 500 | Asn | Ala | Thr | Met | Gln 505 | Cys | Ala | Ala |
| Ser | Phe 510 | Asp | Pro | Ala | Leu | Asp 515 | Leu | Thr | Phe | Val | Trp 520 | Ser | Phe | Asn | Gly |
| Tyr 525 | Val | Ile | Asp | Phe | Asn 530 | Lys | Glu | Asn | Ile | His 535 | Tyr | Gln | Arg | Asn | Phe 540 |
| Met | Leu | Asp | Ser | Asn 545 | Gly | Glu | Leu | Leu | Ile 550 | Arg | Asn | Ala | Gln | Leu 555 | Lys |
| His | Ala | Gly | Arg 560 | Tyr | Thr | Cys | Thr | Ala 565 | Gln | Thr | Ile | Val | Asp 570 | Asn | Ser |
| Ser | Ala | Ser 575 | Ala | Asp | Leu | Val | Val 580 | Arg | Gly | Pro | Pro | Gly 585 | Pro | Pro | Gly |
| Gly | Leu | Arg | Ile | Glu | Asp | Ile | Arg | Ala | Thr | Ser | Val | Ala | Leu | Thr | Trp |

-continued

|     |     |     |     |     | 590 |     |     |     |     | 595 |     |     |     |     | 600 |     |
|-----|-----|-----|-----|-----|-----|-----|-----|-----|-----|-----|-----|-----|-----|-----|-----|-----|
| Ser 605 | Arg | Gly | Ser | Asp 610 | Asn | His | Ser | Pro | Ile 615 | Ser | Lys | Tyr | Thr | Ile 620 | Gln |
| Thr | Lys | Thr | Ile | Leu 625 | Ser | Asp | Asp | Trp 630 | Lys | Asp | Ala | Lys | Thr 635 | Asp | Pro |
| Pro | Ile | Ile | Glu 640 | Gly | Asn | Met | Glu 645 | Ala | Ala | Arg | Ala | Val 650 | Asp | Leu | Ile |
| Pro | Trp | Met 655 | Glu | Tyr | Glu | Phe 660 | Arg | Val | Val | Ala | Thr 665 | Asn | Thr | Leu | Gly |
| Arg | Gly 670 | Glu | Pro | Ser | Ile | Pro 675 | Ser | Asn | Arg | Ile | Lys 680 | Thr | Asp | Gly | Ala |
| Ala 685 | Pro | Asn | Val | Ala 690 | Pro | Ser | Asp | Val | Gly 695 | Gly | Gly | Gly | Arg 700 | Asn |
| Arg | Glu | Leu | Thr | Ile 705 | Thr | Trp | Ala | Pro | Leu 710 | Ser | Arg | Glu | Tyr | His 715 | Tyr |
| Gly | Asn | Asn | Phe 720 | Gly | Tyr | Ile | Val | Ala 725 | Phe | Lys | Pro | Phe | Asp 730 | Gly | Glu |
| Glu | Trp | Lys 735 | Lys | Val | Thr | Val | Thr 740 | Asn | Pro | Asp | Thr | Gly 745 | Arg | Tyr | Val |
| His | Lys 750 | Asp | Glu | Thr | Met | Ser 755 | Pro | Ser | Thr | Ala | Phe 760 | Gln | Val | Lys | Val |
| Lys 765 | Ala | Phe | Asn | Asn | Lys 770 | Gly | Asp | Gly | Pro | Tyr 775 | Ser | Leu | Leu | Ala | Val 780 |
| Ile | Asn | Ser | Ala | Gln 785 | Asp | Ala | Pro | Ser | Glu 790 | Ala | Pro | Thr | Glu | Val 795 | Gly |
| Val | Lys | Val | Leu 800 | Ser | Ser | Ser | Glu | Ile 805 | Ser | Val | His | Trp | Glu 810 | His | Val |
| Leu | Glu | Lys 815 | Ile | Val | Glu | Ser | Tyr 820 | Gln | Ile | Arg | Tyr | Trp 825 | Ala | Ala | His |
| Asp | Lys 830 | Glu | Glu | Ala | Ala | Asn 835 | Arg | Val | Gln | Val | Thr 840 | Ser | Gln | Glu | Tyr |
| Ser 845 | Ala | Arg | Leu | Glu | Asn 850 | Leu | Leu | Pro | Asp | Thr 855 | Gln | Tyr | Phe | Ile | Glu 860 |
| Val | Gly | Ala | Cys | Asn 865 | Ser | Ala | Gly | Cys | Gly 870 | Pro | Pro | Ser | Asp | Met 875 | Ile |
| Glu | Ala | Phe | Thr 880 | Lys | Lys | Ala | Pro | Pro 885 | Ser | Gln | Pro | Pro | Arg 890 | Ile | Ile |
| Ser | Ser | Val 895 | Arg | Ser | Gly | Ser | Arg 900 | Tyr | Ile | Ile | Thr | Trp 905 | Asp | His | Val |
| Val | Ala 910 | Leu | Ser | Asn | Glu | Ser 915 | Thr | Val | Thr | Gly | Tyr 920 | Lys | Val | Leu | Tyr |
| Arg 925 | Pro | Asp | Gly | Gln | His 930 | Asp | Gly | Lys | Leu | Tyr 935 | Ser | Thr | His | Lys | His 940 |
| Ser | Ile | Glu | Val | Pro 945 | Ile | Pro | Arg | Asp | Gly 950 | Glu | Tyr | Val | Val | Glu 955 | Val |
| Arg | Ala | His | Ser 960 | Asp | Gly | Gly | Asp | Gly 965 | Val | Val | Ser | Gln | Val 970 | Lys | Ile |
| Ser | Gly | Ala 975 | Pro | Thr | Leu | Ser | Pro 980 | Ser | Leu | Leu | Gly | Leu 985 | Leu | Leu | Pro |
| Ala | Phe 990 | Gly | Ile | Leu | Val | Tyr 995 | Leu | Glu | Phe |

METHOD FOR DETECTING HUMAN CONTACTIN

This is a division of application Ser. No. 08/040,741, filed Mar. 26, 1993.

FIELD OF THE INVENTION

The present invention relates to cell adhesion molecules and nucleic acid sequences which code for cell adhesion molecules. In particular, the invention pertains to human cell adhesion molecules and nucleic acid sequences which code therefor.

BACKGROUND OF THE INVENTION

Adhesion between cells plays an essential role in development and maintenance of tissue form and function. Intercellular adhesion is mediated by a class of adhesive cell surface proteins commonly referred to as "cell adhesion molecules" or "CAMs". These proteins have been identified and characterized in a phylogenetically diverse range of organisms and have been found in many cases to be highly conserved in structure. Certain cell surface CAMs are members of a superfamily of glycoproteins which are structurally related to immunoglobulins, i.e., their structure contains a number of extracellular immunoglobulin-like and fibronectin Type III-like domains.

The immunoglobulin superfamily of CAMs includes the neural cell adhesion molecule (N-CAM), the L1 antigen, Ng-CAM, TAG-1, and others. These CAMs are believed to mediate homophilic binding between cells and have also recently been recognized as participants in heterophilic interactions with other cell surface molecules, extracellular matrix proteins and proteoglycans. Many are also believed to be involved in transmission of signals to the interior of the cell which modulate cell morphology, cell metabolism and cell adhesion. The means by which these molecules transmit signals to the interior of the cell is unclear.

The F11 antigen (F11) is a chicken neural cell surface-associated glycoprotein which is believed to be involved in neurite-neurite interactions. The cDNA sequence of F 11 has been determined and it codes for a 1010 amino acid protein (Brümmendorf, et al. (1989) Neuron 2:1351-1361). The F11 molecule comprises six domains related to the immunoglobulin domain type C and four domains similar to the fibronectin Type III repeat. These structures are also present in L1 and N-CAM. The cDNA sequence of F11 was found to be almost identical to the cDNA sequence of the chicken neural glycoprotein contactin (Ranscht, et al. (1988) J. Cell Biol. 107:1561-1573; Zisch, et al. (1992) J. Cell Biol. 119:203-213) and it is now believed that the molecules are the same (contactin/F11). However, prior to Applicants' invention, the identity was not clear. A mouse neural cell surface protein, F3, has been identified and is the homologue of the chicken neuronal cell adhesion protein contactin/F11. The cDNA which codes for F3 has been cloned and sequenced, revealing an open reading frame encoding a 1020 amino acid protein having the characteristics of the immunoglobulin superfamily (G. Gennarini, et al. 1989. J. Cell Biol. 109:775-788).

The present invention relates to CAMs involved in human neural cell adhesion. Specifically, the present invention provides the purification and characterization of the human counterpart of the mouse F3 and chicken contactin/F11 proteins, the preparation of monoclonal and polyclonal antibodies to the human contactin and nucleic acid sequences encoding the human contactin. E. Berglund, et al. (1987. J. Neurochem. 48:809-815) have used monoclonal antibodies to characterize glycoproteins in human brain and have reported isolation and characterization of a molecule identified as Gp135 (E. Berglund, et al. 1991. Eur. J. Biochem. 197:549-554; E. Berglund, et al. 1991. Brain Res. 549:292-296). These authors sequenced the amino terminus of the protein and an internal peptide. On the basis of these sequences they identified a similarity to chicken contactin/F11 and mouse F3, however, the reported amino acid sequence of Gp135 is different from that of the human contactin molecule described herein. It was therefore also unclear prior to Applicants' invention whether or not human Gp135 was the direct homolog of F3, contactin/F11. E. Berglund and B. Ranscht later reported the isolation and partial characterization of cDNA clones encoding Gp135 (1992. Soc. Neurosci. Abst. 18:1325, Abst. #560.5).

SUMMARY OF THE INVENTION

Using monoclonal antibodies, a human brain glycoprotein (human contactin) homologous to the mouse F3 and the chicken contactin/F11 adhesion molecules has been isolated and characterized. A complete coding sequence of the human contactin gene has been determined by sequencing of human neuroblastoma cDNA clones. The gene could potentially encode other, alternatively spliced complete coding regions as well. At the nucleotide level, the human cDNA is 86% homologous to the mouse F3 cDNA. The deduced amino acid sequences are 95% homologous and predict several common structural features, including six immunoglobulin-like and four fibronectin Type III-like domains, as well as multiple sites for Asn-linked glycosylation. The mouse, chicken and human glycoproteins all contain carboxy-terminal hydrophobic segments which may be important for linking the proteins to the cell surface via a phosphatidylinositol anchor.

The human contactin glycoprotein is approximately 135 kD molecular weight and may be purified by immunoaffinity methods using monoclonal antibodies. Partial sequencing of an internal peptide yielded an amino acid sequence identical to that predicted from the cDNA. The cDNA has been expressed in recombinant host microorganisms and the gene product has been shown to be immunoreactive with polyclonal antisera raised against the monoclonal antibody-purified human contactin antigen. Northern blot analyses of the RNAs of various human tissues demonstrated a single major approximately 6.5 kb human contactin transcript in adult brain. Multiple transcripts (6.8 kb, a 6.0 kb doublet and 4.2 kb) are expressed in retinoblastoma and neuroblastoma cell lines. A low level expression of approximately 6.8 and 6.0 kb transcripts, similar to those observed in transformed cell lines, was also detected in human lung and pancreas. Very weak 6.8 and 6.0 kb bands were seen in kidney and skeletal muscle.

DETAILED DESCRIPTION OF THE INVENTION

Figure 1:
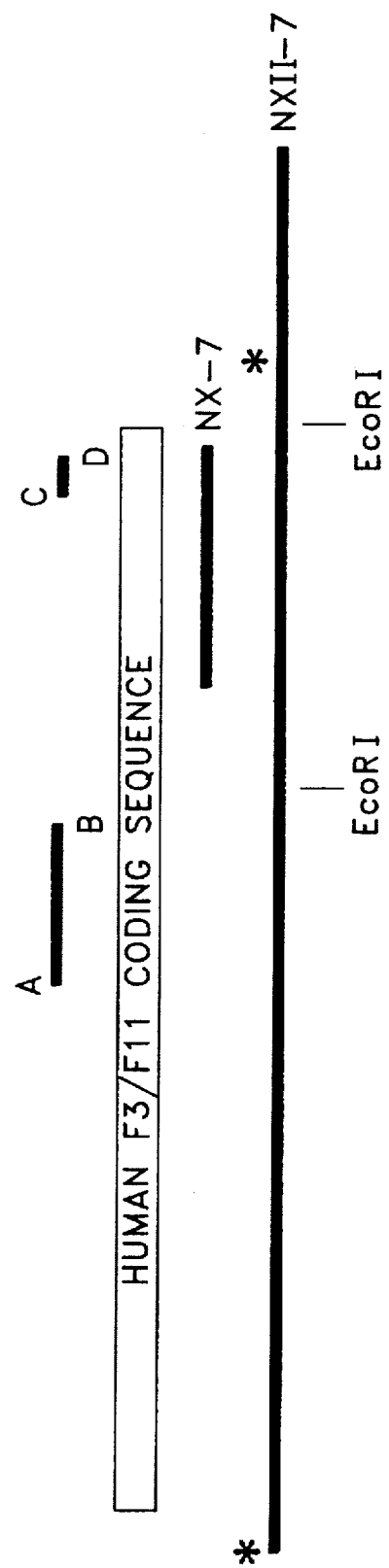
FIG. 1 illustrates the relationships of the mouse F3 probes used to clone the human contactin cDNA, the cDNAs carried in the NX-7 and NXII-7 clones and the human contactin coding sequence.

The human contactin cell adhesion protein of the invention may be isolated from any human neural tissue in which it is expressed. The preferred source is human brain tissue. While conventional chemical and biochemical methods for isolation may be employed, the human contactin cell adhesion protein is most preferably isolated by immunoaffinity methods using antibodies which recognize and bind to it. Immunoaffinity methods for isolating antigens are well known in the art and may be employed to isolate the human contactin of the present invention using the appropriate monoclonal or polyclonal antibody which recognizes the human contactin molecule. Monoclonal antibodies such as the CF3 antibody described by E. Berglund, et al., supra, or the Neuro-1 antibody described below are preferred, the Neuro-1 antibody being most preferred for isolation of the human contactin protein.

Monoclonal antibodies which recognize the human contactin protein of the invention may be prepared using the methods of Kohler and Milstein ((1975) Nature 256:495) as is known in the art. The preferred antigen for immunization is a preparation of adult human brain membranes and the most preferred antigen is a synaptosomal fraction of these membranes which is enriched for cell surface glycoproteins. Mice may be immunized with the antigen preparation, the spleen cells fused and the resulting hybridomas screened against the original immunogen to select hybridomas.

Using these methods, a hybridoma which produces the monoclonal antibody herein designated Neuro-1 was identified. A crude synaptosomal membrane fraction was prepared from adult human brain tissue (Carlin, R. K., et al. (1980) J. Cell. Biol. 86:831–843)). Membrane glycoproteins were extracted with TERGITOL Type NP-40 (polyglycol ether surfactant, Union Carbide Corp.) and separated by affinity chromatography on immobilized lentil lectin (Pharmacia Biotech, Inc., Piscataway, N.J.) to yield a crude brain glycoprotein fraction. This material was used to immunize C57BL/6 mice (40 µg/mouse). Lymph nodes from animals having the highest serum titers against the immunogen were fused with PcX63Ag8.653 cells (Coding, J. W. (1980) J. Immun. Meth. 39:285–308; ATCC CRL 1580). The resulting hybridomas were screened in enzyme-linked immunosorbent assays (ELISAs) for reactivity with the immunogen and tested for reactivity in immunoblots. A hybridoma secreting an antibody designated Neuro-1 was subcloned by limiting dilution. The Neuro-1 monoclonal antibody was produced in ascites in pristane-primed Balb/C mice and purified by chromatography on Protein A-Sepharose (Sigma Chemical Co., St. Louis, Mo.).

Neuro-1, isotype IgG2b, reacts strongly with the original immunogen in enzyme-linked immunosorbent assays (ELISAs) and recognizes an approximately 135 kD polypeptide on immunoblots. Occasionally, the Neuro-1 antigen appears on immunoblots as a closely spaced doublet. The Neuro-1 producing hybridoma has been deposited with the American Type Culture Collection (12301 Park-lawn Drive, Rockville, Md.) on Mar. 3, 1993 under the Accession Number HB 11282 and it is the preferred monoclonal antibody for isolation and characterization of the human contactin cell adhesion molecule.

Neuro-1 monoclonal antibody was coupled to Protein A-Sepharose using methyl piperimidate (Harlow, E. and Lane, D. (1988) *Antibodies: A Laboratory Manual*, Cold Spring Harbor Press, p. 522). The membrane extracts described above were then passed over the affinity column and the bound antigen eluted using 0.1M diethylamine, pH 11.5. The eluted material was concentrated by binding to diethylaminoethyl cellulose (Whatman DE52, Fisher Scientific, Pittsburgh, Pa.) in 0.01M Tris-HCl and eluted with 1M NaCl. It was found that if frozen membrane extracts were used in the isolation procedure the Neuro-1 antigen tended to become insoluble. In these cases, the precipitated material was solubilized in deoxycholate, dialyzed against NP40-containing column buffer and processed as above.

Polyclonal antibodies were generated by immunizing animals with the material bound and eluted from immobilized Neuro-1 affinity columns. The polyclonal antibodies were further enriched by chromatography on an immobilized Neuro-1 antigen affinity column.

The 135 kD Neuro-1 antigen was characterized by binding to lentil lectin-Sepharose and elution with glucose, indicating that the polypeptide is glycosylated. The presence of asparagine-linked carbohydrate was verified by treating the antigen with endoglycosidase F (Genzyme, Cambridge, Mass.) and showing a shift to a lower molecular weight. The antigen was found to be released from the cell surface by phosphatidylinositol-specific phospholipase C, indicating that the molecule is anchored to the surface by a lipid linkage. These analyses were performed by washing crude human brain synaptosomal membrane preparations and suspending them in 0.02M NaOAc, pH 6.0. The enzyme was added and the samples were incubated for 4 hours at 37° C. The membranes were collected by centrifugation and equivalent amounts of membranes and supernatants were analyzed by immunoblotting. Treatment of the reaction mixtures with zinc or with o-phenanthrolene showed inhibition and no inhibition of release, respectively. Both polypeptides of the doublet seen on immunoblots were released by phospholipase C treatment, so it is believed that they do not represent anchored and endogenously released forms of the human contactin molecule.

The amino terminal sequence and the sequence of an internal peptide of the Neuro-1 antigen were determined and compared to the published amino acid sequences of mouse F3 and chicken contactin/F11. Amino terminal sequences were determined using immunoaffinity purified material blotted to IMMOBILON-P (Pall Corp., Glen Cove, N.Y.). The amino terminal sequence data were difficult to interpret and contained a large number of unassigned residues. Although many of these ambiguities involved amino acids which are sometimes difficult to detect by sequence analysis, it is also possible that proteolysis of the molecule creates heterogeneity at the amino terminus. Internal peptides were generated by cleavage with endopeptidase lys-c, separated by HPLC and sequenced. The sequence of the internal peptide was clear and was found to be very similar to peptides in F3 and contactin/F 11. In addition, because the human peptide was generated by endopeptidase lys-c cleavage, it is most likely flanked by lysine residues. These residues are also conserved in mouse and chicken. On the basis of the amino acid sequence similarities, it is believed that the Neuro-1 antigen is the human counterpart of F3 and contactin/F11. It is therefore referred to herein as human contactin.

cDNAs encoding the Neuro-1 antigen were cloned to confirm its identity as human contactin. Mouse F3 probes were used to screen a human neuroblastoma cDNA library (Clontech, Palo Alto, Calif.). The probes were generated by reverse transcriptase-polymerase chain reaction (RT-PCR) of mouse brain polyA+RNA using primer pairs based on the mouse F3 sequence as reported by Gennarini, et al. supra, (GENBANK locus: musF3, accession #X14943). To perform the RT-PCR, mouse brain polyA+RNA was prepared using the oligo d(T) cellulose method (Maniatis, et al. *Molecular Cloning—A Laboratory Manual*, Cold Spring Harbor Laboratory, 1982). The RT-PCR amplification reaction was based on the one-step protocol described by Goblet, et al. (1989. Nucleic Acids Res. 17:2144). PolyA+RNA (1

μg) and 300 ng of each primer (see below) in 66 μl DEPC water were incubated at 65° C. for 15 min. and cooled on ice. Thirty-three gl of 3X RT-PCR reagent mix (3× X PCR buffer, 150 mM KCl, 30 mM Tris-Cl pH 8.3, 4.5 mM MgCl₂, 0.3% gelatin, 500 μM dNTPs, 200 U M-MLV reverse transcriptase, 4 U rRNAsin (Promega, Madison, Wis.), 2.5 U AMPLITAQ (Perkin-Elmer Cetus, Norwalk, Conn.) was added and the reaction was incubated at 37° C. for 30 min., followed by 94° C. for 1 min, 50° C. for 2 min., and 72° C. for 2 min. The amplification reaction was repeated for 40 cycles. Primer pairs A/B and C/D were used for amplification of the mouse F3 probes:

| PRIMER FIG. 1 | SEQUENCE ID NO. | SEQUENCE* | NUCLEOTIDE POSITION IN musF3 |
|---|---|---|---|
| A | SEQ ID NO: 3 | CTCTGGTGATCACAAATC | 1742–1759 |
| B | SEQ ID NO: 4 | TCATCTGAGAGAATCGTC | 2181–2198 |
| C | SEQ ID NO: 1 | TAGACCGGATGGCCAACA | 3087–3104 |
| D | SEQ ID NO: 2 | CTCGACAACATACTCTCC | 3163–3180 |

*Primers B and D are inverse complements of musF3.

The probes were verified as mouse F3 by direct sequencing with SEQUENASE (United States Biochemical Corp., Cleveland, Ohio) performed as described by Mihovilovic ((1989) BioTechniques 7: 14–16). This is an efficient method for sequencing PCR amplified DNA. The PCR products of primer pair SEQ ID NO: 1/SEQ ID NO:2 (94 bp) and SEQ ID NO:3/SEQ ID NO:4 (457 bp) were gel purified and re-amplified using asymmetric primer concentrations to produce the single-stranded sequencing templates.

Using the mouse SEQ ID NO: 1/SEQ ID NO:2 probe prepared above, a human Kelly neuroblastoma lambda gt10 cDNA library (Clontech, Palo Alto, Calif.) was screened as recommended by the manufacturer. Two cDNA clones were isolated, including the clone NX-7 which contained the cDNA shown in FIG. 1. To obtain clones containing upstream sequences, the neuroblastoma library was screened using the mouse SEQ ID NO:3/SEQ ID NO:4 probe. Three clones were identified from this screening, including one which was a full-length clone containing the entire coding sequence. This clone was designated clone NXII-7. Lambda cDNA inserts were either PCR amplified using lambda gt10 EcoRI forward and reverse primers and sequenced directly or subcloned into pBLUESCRIPT (SK+) (Stratagene, La Jolla, Calif.) prior to sequencing. The pBLUESCRIPT subclones were sequenced manually by either dideoxy termination with SEQUENASE or by dye-termination or dye-labeled primer automated sequencing (Applied Biosystems, Model 373A, Foster City, Calif.) as recommended by the manufacturers. Sequencing primers were synthesized on an Applied Biosystems (ABI) Model 380B DNA synthesizer and purified using OPC cartridges (ABI) as recommended. Sequence alignments, translations, and features location were performed using IG-Suite software (Intelligenetics, Mountain View, Calif.). The cDNAs produced by this procedure may be used as probes to isolate the genomic DNA coding for human contactin.

The entire human contactin cDNA coding and partial 5' and 3' untranslated sequence was determined by sequencing both strands of cDNAs (SEQ B NO:5; EMBL Accession #Z21488). Among the various cDNA clones, two single base variations were observed at positions 2424 and 2513. These result in valine to alanine and leucine to valine transitions, respectively. Human contactin cDNA contains a 3054 bp open reading frame which is capable of encoding a polypeptide 1018 amino acids in length (SEQ NO:6). The predicted polypeptide contains hydrophobic segments at the amino-terminal and carboxyl-terminal ends. The amino terminal hydrophobic segment contains a consensus processing site and is believed to be a signal sequence which is cleaved to yield the amino terminus of the mature polypeptide. The hydrophobic segment at the carboxyl terminus is similar to segments found at the carboxyl ends of other phosphatidylinositol-linked membrane proteins and it is believed to be removed during the attachment to glycolipid. The fact that the Neuro-1 antigen is released from the cell surface by phosphatidylinositol-specific phospholipase C is consistent with this hypothesis. Included in the predicted amino acid sequence of the polypeptide, at positions 836–850, is the sequence of the Neuro-1 antigen lys-c peptide described above, confirming that the Neuro-1 antigen is the human contactin cell adhesion molecule.

As previously disclosed, Berglund, et al. have reported a molecule designated Gp135 which they describe as a possible human homologue of mouse F3 and chicken contactin/F11. However, the Berglund, et al. internal peptide sequence is only 71% similar to the deduced amino acid sequence of a corresponding peptide (residues 679–693) of the present invention.

The deduced amino acid sequence of human contactin contains six immunoglobulin-like domains followed by four fibronectin Type III-like repeats. This structure is similar to mouse F3 and chicken contactin/F11. In the second fibronectin Type III repeat the carboxyl-terminal conserved tyrosine is replaced by phenylalanine as in mouse F3. There are nine consensus sites for asparagine-linked glycosylation, all of which are conserved between human and mouse. The deduced human and mouse polypeptide sequences are 95% homologous and differ in size by two amino acids. Mouse F3 contains a single dipeptide insert within the sixth immunoglobulin-like domain which is absent in human contactin and chicken contactin/F11. It is not known whether this sequence gap is the result of alternate RNA splicing or a reflection of intra-exonic differences between species. The regions of lowest sequence identity have about 70% homology and are located in the hydrophobic amino terminal and carboxyl-terminal segments.

Polyclonal antisera were generated in rabbits using immunoaffinity purified human contactin to further confirm that the Neuro-1 antigen is the human homologue of F3 and contactin/F11. The sera recognized the immunogen in immunoblots at a 1:12,000 dilution. The sera also reacted with a gultathione S-transferase/human contactin fusion protein expressed in bacteria. The human contactin portion of this fusion protein comprised the carboxy-terminal region of human contactin, corresponding to the cDNA in clone NX-7, cloned in pGEX-2T (Pharmacia, Piscataway, N.J.).

The upstream EcoRI fragment of the cDNA insert of NXII-7 and the entire cDNA insert of NX-7 were used as probes to characterize the expression pattern of human contactin in various tissues. Human brain contained a single major approximately 6.5 kb mRNA. This transcript is larger than is necessary to encode the human contactin protein and is believed to include a large 3' untranslated region which is not completely represented in the cDNA clones isolated. The isolated cDNAs extended no more than about 1.2 kb past the carboxyl-terminus of the human contactin molecule.

Of the other tissues tested, pancreas and lung exhibited a low level of expression (compared to brain) of the 6.8 kb transcript and a 6.0 kb doublet similar to the pattern seen in cell lines (see below). Skeletal muscle and kidney showed similar, yet very weak 6.8 and 6.0 kb transcripts. Heart and liver were negative for human contactin transcripts. The human neuroblastoma cell lines IMR-32, SK-N-MC, SMS-KAN and SK-N-SH contained human contactin mRNA as did the retinoblastoma cell line Y79. In these cell lines, in contrast to the transcript pattern in brain, multiple RNA species were observed—a 6.8 kb species, a 6.0 kb doublet and a 4.2 kb species. It is unclear in all cases whether or not the approximately 6.8 kb and 6.5 kb transcripts are significantly different. Rhabdomyosarcoma (A204, RD and A673), hematopoietic KGla, 5), small cell lung carcinoma (SHP77) and Ewing Sarcoma RD-ES) cell lines did not express human contactin RNA.

The antibodies which recognize human contactin and the nucleotide probes derived from the nucleotide sequence which codes for human contactin are useful in methods for detecting the protein and nucleotide sequences, respectively. Nucleotide probes may comprise the complete cloned cDNA sequence or a portion thereof. One skilled in the art will further recognize that nucleotide probes may be designed which comprise all or a portion of a sequence which is complementary to the cloned sequences. To detect the contactin protein, immunoassay methods involving binding between a protein and its antibody such as ELISAs and immunoblots can be readily adapted to employ the antibodies and contactin glycoprotein disclosed herein. These immunoassay methods are known in the art. In general, detection of binding between protein and antibody is accomplished by including a signal moiety in the binding reaction. This is usually in the form of a detectable label conjugated to the antibody or protein. The detectable label may be directly detectable (e.g., a dye, radioisotope or fluorochrome) or rendered detectable after further chemical reaction (e.g., an enzyme which reacts to produce a colored product or biotin which may be bound to labeled avidin).

Detection of nucleic acids by hybridization to a probe is also known in the art. Such methods as Southern blotting, dot blotting and the like may be readily adapted to detection of oligonucleotides containing all or part of a nucleic acid sequence encoding human contactin using the nucleotide sequence information of SEQ ID NO:5 to design appropriate probes. For purposes of the present invention, the terms "encoding" and "coding for" are intended to include nucleic acids which comprise sequences which can be transcribed and/or translated to produce human contactin. That is, both DNA and the RNA transcribed from it are considered to "code for" or "encode" human contactin. It will also be understood that probes derived from the disclosed nucleotide sequences may also be used to detect fragments of the disclosed coding sequences. As for immunoassays, hybridization of the probe to the contactin nucleotide sequence will be detected by means of a directly or indirectly detectable label associated with the probe, i.e., incorporated in the probe or conjugated to it. In general the same labels useful for labeling antibodies and antigens may be used to label oligonucleotides. In addition, it is within the ordinary skill in the art, given the nucleotide sequence of SEQ ID NO:5, to derive the complementary nucleotide sequence, which may also be used to prepare probes and which may be detected by hybridization to probes. Further, the present disclosure of SEQ ID NO:5 as a DNA sequence easily allows derivation of RNA sequences which are complementary to either SEQ ID NO:5 or its complementary strand. Such equivalent RNA sequences may be detected by hybridization to probes as well.

The reagents for performing these immunoassays and hybridization assays may be conveniently packaged together for sale or use in the form of a kit. A kit for immunoassay may contain an antibody which recognizes and binds to human contactin conjugated to a selected label and optionally any reagents necessary for performing the assay and detecting the label. A kit for a hybridization assay may contain short oligonucleotide probes which hybridize to one or more nucleotide sequences contained in SEQ ID NO:5, the probes being conjugated to the selected label. Optionally, the hybridization assay kit may contain any reagents necessary for performing the hybridization assay and detecting the label.

The foregoing disclosure is intended to illustrate the invention but is not to be construed as limiting its scope as defined by the appended claims. Upon reading the present disclosure, certain equivalents and variations will be apparent to one skilled in the art without the exercise of inventive skill and without departing from the spirit of the invention. Such equivalents and variations are intended to be included within its scope.

What is claimed is:

1. A method for detecting human contactin in a sample comprising contacting the sample with monoclonal antibody Neuro-1 produced by hybridoma ATCC No. HB11282, under conditions suitable for binding of the Neuro-1 antibody to the human contactin and detecting binding of the Neuro-1 antibody.

2. The method of claim 1 wherein antibody binding is detected by means of a detectable label conjugated to the Neuro-1 antibody.

3. The method of claim 1 wherein the Neuro-1 antibody is produced by hybridoma ATCC No. HB11282.

4. A kit of materials for detecting human contactin in a sample comprising, in an enclosure, a monoclonal antibody Neuro-1 produced by hybridoma ATCC No. HB11282, and a means for detecting binding of the Neuro-1 antibody to the human contactin.

5. The kit of claim 4 wherein the means for detecting binding comprises a detectable label conjugated to the Neuro-1 antibody.

* * * * *